United States Patent
Lee et al.

(10) Patent No.: US 11,118,060 B2
(45) Date of Patent: Sep. 14, 2021

(54) COMPOSITE WHITE PIGMENT

(71) Applicant: CQV CO., LTD., Chungcheongbuk-do (KR)

(72) Inventors: Jin-Hyoung Lee, Cheongju-si (KR); Kwang-Choong Kang, Cheongju-si (KR); Byung-Ki Choi, Cheongju-si (KR); Kwang-Soo Lim, Cheongju-si (KR); Kil-Wan Chang, Cheongju-si (KR)

(73) Assignee: CQV CO., LTD., Chungcheongbuk-Do (KR)

( * ) Notice: Subject to any disclaimer, the term of this patent is extended or adjusted under 35 U.S.C. 154(b) by 34 days.

(21) Appl. No.: 16/493,002

(22) PCT Filed: Mar. 27, 2018

(86) PCT No.: PCT/KR2018/003567
§ 371 (c)(1),
(2) Date: Sep. 11, 2019

(87) PCT Pub. No.: WO2018/194284
PCT Pub. Date: Oct. 25, 2018

(65) Prior Publication Data
US 2020/0071534 A1    Mar. 5, 2020

(30) Foreign Application Priority Data
Apr. 21, 2017 (KR) .................. 10-2017-0051789

(51) Int. Cl.
| | |
|---|---|
| *C09C 1/00* | (2006.01) |
| *C09D 7/40* | (2018.01) |
| *C09D 7/62* | (2018.01) |
| *A61K 8/25* | (2006.01) |
| *A61K 8/29* | (2006.01) |
| *A61K 8/34* | (2006.01) |
| *A61K 8/81* | (2006.01) |
| *A61K 8/92* | (2006.01) |
| *A61Q 1/06* | (2006.01) |
| *C09D 167/00* | (2006.01) |

(52) U.S. Cl.
CPC ............ *C09C 1/0024* (2013.01); *A61K 8/25* (2013.01); *A61K 8/29* (2013.01); *A61K 8/342* (2013.01); *A61K 8/8182* (2013.01); *A61K 8/922* (2013.01); *A61Q 1/06* (2013.01); *C09D 7/62* (2018.01); *C09D 7/70* (2018.01); *C09D 167/00* (2013.01); *C01P 2004/20* (2013.01); *C01P 2004/84* (2013.01); *C01P 2006/60* (2013.01); *C09C 2200/102* (2013.01); *C09C 2200/301* (2013.01); *C09C 2200/302* (2013.01); *C09C 2200/308* (2013.01); *C09C 2210/60* (2013.01); *C09C 2220/106* (2013.01)

(58) Field of Classification Search
None
See application file for complete search history.

(56) References Cited

U.S. PATENT DOCUMENTS

| | | | |
|---|---|---|---|
| 6,596,070 B1 * | 7/2003 | Schmidt ............... | C09C 1/0039 106/417 |
| 6,787,633 B2 | 9/2004 | Peemans et al. | |
| 2004/0221770 A1 | 11/2004 | Schmidt et al. | |
| 2006/0051304 A1 | 3/2006 | Peng et al. | |

FOREIGN PATENT DOCUMENTS

| | | |
|---|---|---|
| CN | 1302314 A | 7/2001 |
| CN | 1732234 A | 2/2006 |
| CN | 1738870 A | 2/2006 |
| DE | 10313978 A1 | 10/2004 |
| EP | 01586296 A1 | 10/2005 |
| EP | 2980173 A1 | 2/2016 |
| JP | 09-067527 A | 3/1997 |
| JP | 2000-001628 A | 1/2000 |
| JP | 2000-198944 A | 7/2000 |
| JP | 2000-319540 A | 11/2000 |
| JP | 2001-520296 A | 10/2001 |
| JP | 2002-155242 A | 5/2002 |
| JP | 2002-516375 A | 6/2002 |
| JP | 2002-524647 A | 8/2002 |
| JP | 2002-275423 A | 9/2002 |
| JP | 2003-171575 A | 6/2003 |
| JP | 2004-269892 A | 9/2004 |
| JP | 2005-502738 A | 1/2005 |
| JP | 2005-068186 A | 3/2005 |
| JP | 2005-272745 A | 10/2005 |
| JP | 2006-045562 A | 2/2006 |
| JP | 2006-522165 A | 9/2006 |
| JP | 2009-536231 A | 10/2009 |
| JP | 2012-237003 A | 12/2012 |
| JP | 2013-177639 A | 9/2013 |
| JP | 2015-211334 A | 11/2015 |

(Continued)

OTHER PUBLICATIONS

International Search Report dated Jul. 17, 2018 for corresponding international application No. PCT/KR2018/003567.

(Continued)

*Primary Examiner* — Nannette Holloman
(74) *Attorney, Agent, or Firm* — Hauptman Ham, LLP

(57) ABSTRACT

Disclosed is a composite white pigment having mixed together white pigments having different colorimeter values from each other by comprising substrates having various sizes and/or TiO2 having various thicknesses. The composite white pigment, according to the present invention, comprises: a first white pigment comprising a substrate and a white metal oxide layer formed on the substrate; and a second white pigment comprising a substrate and a white metal oxide layer formed on the substrate, and having a different colorimeter value from that of the first white pigment.

12 Claims, 1 Drawing Sheet

(56) References Cited

FOREIGN PATENT DOCUMENTS

| JP | 2018-126136 A | 8/2018 |
|---|---|---|
| KR | 10-2001-0024014 A | 3/2001 |
| KR | 10-1104593 B1 | 1/2012 |
| KR | 10-2012-0107013 A | 9/2012 |
| KR | 10-2015-0135465 A | 12/2015 |

OTHER PUBLICATIONS

Japanese Office Action dated Aug. 25, 2020, in connection with the Japanese Patent Application No. 2019-549011.
Extended European Search Report dated Aug. 3, 2020, in connection with the counterpart European Patent Application No. EP18788241.0.
Chinese Office Action dated Sep. 25, 2020, in connection with the Chinese Patent Application No. 201880016802.8.
Chinese Notice of Allowance dated Apr. 19, 2021, in connection with the Chinese Patent Application No. 201880016802.8.

* cited by examiner

COMPOSITE WHITE PIGMENT

CROSS-REFERENCE TO RELATED APPLICATION

The present application is a national stage filing under 35 U.S.C § 371 of PCT application number PCT/KR2018/003567 filed on Mar. 27, 2018 which is based upon and claims the benefit of priority to Korean Patent Application No. 10-2017-0051789 filed on Apr. 21, 2017, in the Korean Intellectual Property Office, which is incorporated herein in its entirety by reference.

TECHNICAL FIELD

The present disclosure relates to pigment producing techniques, and more particularly to a composite white pigment capable of exhibiting high gloss and whiteness.

BACKGROUND ART

White pigments are used for aesthetic effect in various fields. For example, the white pigment is used in industrial applications such as wallpaper, floor plate, plastic molding, leather coating, silk printing, offset printing, painting of household appliances and application of ceramics. For cosmetics, the white pigment is used in various color cosmetics such as lipstick, nail polish, hair gel, eye shadow, and lip closure. In addition, pearl pigments are used in automotive interior and exterior painting, construction, and ship paint that require high weather resistance.

A typical white pigment has a structure in which a metal oxide such as $TiO_2$ having 60 to 100 nm thickness is coated on a plate substrate having about 350 to 700 nm thickness and made of mica.

However, the white pigment having such a structure has a disadvantage in that it lacks gloss or has low whiteness, resulting in lack of white aesthetics.

Prior Art Literature (Patent Document 1) Patent Document 1: Korean Patent Application Publication No. 10-2012-0107013 (published on Sep. 27, 2012)

DISCLOSURE

Technical Purposes

A purpose of the present disclosure is to realize a composite white pigment including a substrate having a specific thickness and a metal oxide layer having a specific thickness, in which a ratio therebetween is controlled to provide an excellent gloss and white degree.

Technical Solutions

In one aspect of the present disclosure, there is provided a composite white pigment comprising: a first white pigment including a substrate and a white metal oxide layer formed on the substrate; and a second white pigment including a substrate and a white metal oxide layer formed on the substrate, wherein the second white pigment has a colorimeter value different from a colorimeter value of the first white pigment.

In a first embodiment of a composite white pigment, the composite white pigment includes a first white pigment including a substrate and a white metal oxide layer formed on the substrate; and a second white pigment including a substrate and a white metal oxide layer formed on the substrate, wherein the first and second pigments are mixed with each other, wherein a minimum thickness of the metal oxide layer of the second white pigment is greater by 50 nm or greater than a maximum thickness of the metal oxide layer of the first white pigment.

In a second embodiment of a composite white pigment, the composite white pigment includes a first white pigment including a substrate and a white metal oxide layer formed on the substrate; and a second white pigment including a substrate and a white metal oxide layer formed on the substrate, wherein the first and second pigments are mixed with each other, wherein a minimum thickness of the second white pigment is greater by 50 nm or greater than a maximum thickness of the first white pigment.

In this connection, the first white pigment includes the white metal oxide layer having a thickness of 30 to 80 nm, and the second white pigment includes the white metal oxide layer having a thickness of 60 to 100 nm.

In a third embodiment of a composite white pigment, the composite white pigment includes a first white pigment including a substrate and a white metal oxide layer formed on the substrate; and a second white pigment including a substrate and a white metal oxide layer formed on the substrate, wherein the first and second pigments are mixed with each other, wherein the white metal oxide layer includes: a first high refractive layer formed on a surface of the substrate and containing $TiO_2$; a low-refractive layer formed on the first high refractive layer and containing a material having a refractive index lower than a refractive index of $TiO_2$; and a second high refractive layer formed on the low-refractive layer and containing $TiO_2$, wherein when a thickness of the first high refractive layer is T1 and a thickness of the second high refractive layer is T2, $2T1>T2≥T1$ for the first white pigment, while $3T1≥T2≥2T1$ for the second white pigment.

In this connection, the composite white pigment may include at least two groups of substrates having thickness differences of at least 50 nm therebetween.

Further, each of the first high refractive layer and the second high refractive layer may contain $TiO_2$ having a rutile structure. The low-refractive layer contains at least one of $SiO_2$ and $MgO.SiO_2$.

In above embodiments, the substrate may be selected from natural mica, synthetic mica, glass flake and alumina flake.

The composite white pigment according to the present disclosure may be contained as an interference pigment in various articles such as cosmetics, paints, plastics.

Technical Effects

The white pigment according to the present disclosure contains the substrate with a specific thickness and the metal oxide layer with a specific thickness, in which white pigments with different colorimeter values are mixed with each other to realizes the white pigment having excellent gloss and whiteness.

In addition, relative thickness control between the high-refractive layers such that the second high-refractive layer as an upper layer is thicker than the first high-refractive layer as a lower layer, and adjusting of the thickness of the upper second high refractive layer to the thickness of the lower first high refractive layer may allow the white pigment of various tones to a red tone from a green tone to be easily produced at the specific thickness of the substrate.

DETAILED DESCRIPTIONS

The advantages and features of the present disclosure, and how to accomplish them, will become apparent with reference to the embodiments described in detail below. However, the present disclosure is not limited to the embodiments disclosed below, but may be implemented in various different forms. Those embodiments are provided only to allow the present disclosure to be complete, and to allow the scope of the invention to be known to those skilled in the art to which the present disclosure pertains. The scope of the present disclosure is only defined by the claims.

Hereinafter, a composite white pigment according to the present disclosure will be described in detail with reference to the accompanying drawings.

Figure 1:
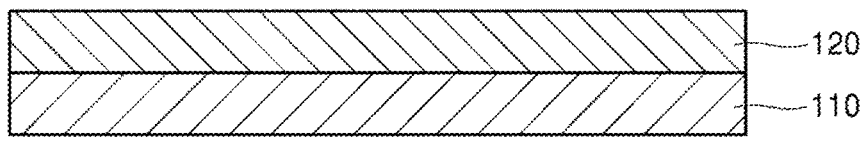
FIG. 1 is a schematic representation of a white pigment according to Comparative Example 1 of the present disclosure.

FIG. 1 is a schematic representation of a white pigment in accordance with the present disclosure.

Referring to FIG. 1, the illustrated white pigment has a structure in which a white metal oxide layer 120 such as a $TiO_2$ layer is formed on a substrate 110.

Figure 2:
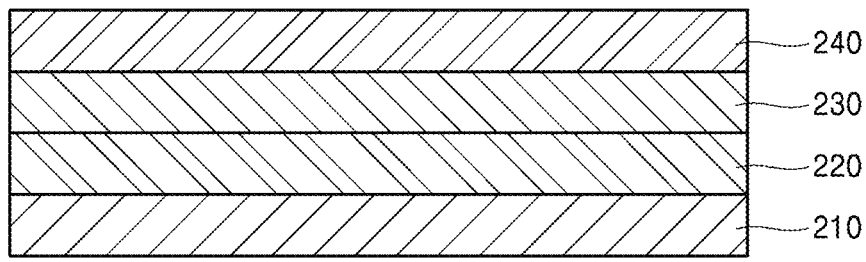
FIG. 2 is a schematic representation of a white pigment according to Present Example 3 of the present disclosure.
Figure 3:
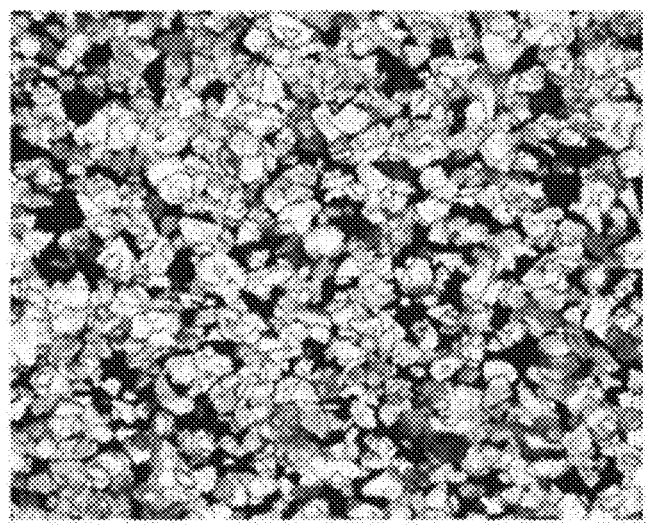
FIG. 3 shows an optical microscope (500 magnification) photograph of the white pigment according to Present Example 3.

FIG. 2 outlines another white pigment in accordance with the present disclosure.

Referring to FIG. 2, the illustrated white pigment has a structure in which a multilayered white oxide layer is formed on a substrate 210. The multilayered white oxide layer has a stack of a lower $TiO_2$ layer as a first high refractive layer 220, a middle low-refractive layer 230 such as a $SiO_2$ layer, and a second high refractive layer 240 such as an upper $TiO_2$ layer.

In the white pigment having the structure shown in FIG. 2, since the $SiO_2$ layer 230 is present as the middle layer, the gloss of the pigment can be improved.

Referring to FIG. 1 and FIG. 2, the white pigment according to the present disclosure includes the substrate 110 or 210, and the white metal oxide layer composed of at least one layer 120 or 220 to 240 formed on the substrate 110 or 210. The white metal oxide actually covers an entire surface of the substrate. However, for the sake of simplicity, the white metal oxide layer is shown to be formed on the substrate in FIG. 1 and FIG. 2.

The substrate 110 or 210 may be made of a material selected from natural mica, synthetic mica, glass flake and alumina flake. The substrate is preferably a plate-like substrate in terms of a shape. In another example, the substrate may be embodied as a spherical substrate. In one example, the length of the substrate 110 or 210 in the longitudinal direction thereof may be in a range of about 5 to 600 μm.

In the embodiment shown in FIG. 2, a stack of the second high refractive layer 240, the middle low-refractive layer 230, and the first high refractive layer 220 in this order may not be plural but may be single. In another example, the stack of the second high refractive layer 240, the middle low-refractive layer 230, and the first high refractive layer 220 may be repeatedly formed two or more times, if necessary. In addition, each of additional coating layers may be further formed between the coating layers, that is, the second high refractive layer 240, the middle low-refractive layer 230, and the first high refractive layer 220. In one example, a protective coating layer may be further formed on the upper second high refractive layer 240 for the purpose of improving weatherability. Further, in the embodiment shown in FIG. 1 and FIG. 2, a pretreatment layer made of tin chloride $SnCl_4$ or the like may be further formed on the substrate before forming the white metal oxide layer.

Hereinafter, the structure of the white pigment according to the embodiment shown in FIG. 2 will be described in more detail.

The first high refractive layer 220 is formed on the surface of the substrate 210 and contains $TiO_2$.

In accordance with the present disclosure, the upper second high refractive layer 240 acts as the main layer for the white rendering. The lower first high refractive layer 220 contributes to enhancing the whiteness. The thickness of the first high refractive layer 220 may be in a range of 30 to 90 nm, but is not limited thereto.

Further, $TiO_2$ contained in each of the first high refractive layer 220 and the second high refractive layer 240 may have rutile or anatase structure. It is more preferable for $TiO_2$ to have a rutile structure. When using the rutile $TiO_2$, there occurs an advantage that the pigment is more excellent in the gloss and stability thereof than when using $TiO_2$ in the anatase structure. The first high refractive layer and the second high refractive layer including the rutile $TiO_2$ may be formed by pretreating the substrate surface with a tin compound such as $SnCl_4$ and then coating $TiO_2$ on the treated surface using $TiCl_4$ or the like.

The low-refractive layer 230 is formed on the first high refractive layer 220.

The low-refractive layer 230 is located between the first high refractive layer 220 and the second high refractive layer 240 to form an optical interference structure, thereby contributing to enhancement of white intensity. The low-refractive layer may include at least one of $SiO_2$ and $MgO.SiO_2$.

The second high-refractive layer 240 is formed on the low-refractive layer 230. In this connection, it is preferable that a thickness of the second high refractive layer 240 is equal to or larger than the thickness of the lower first high refractive layer 220. That is, when the thickness of the first high refractive layer is T1 and the thickness of the second high refractive layer is T2, it is preferable that T2 is equal to or larger than T1. This is because that when the first high refractive layer is thicker than the second high refractive layer, the whiteness is lowered to disallow the white rendering, and when the two layer have the same thickness, the hiding ability is reduced and a merit of the resulting pigment is slightly lowered.

In one example, each of the first high refractive layer and the second high refractive layer may be formed from $TiCl_4$ under strongly acidic conditions lower than or equal to pH 3.

In one example, the low-refractive layer may be made of $SiO_2$ or $MgO.SiO_2$. More specifically, a neutral condition of pH 6 to 8 is maintained when $SiO_2$ or $MgO.SiO_2$ is added. Then, after $SiO_2$ or $MgO.SiO_2$ has been added, a strongly acidic condition lower than or equal to pH 3 may be maintained.

The composite white pigment according to the present disclosure may contain a mixture of a first white pigment and a second white pigment.

The first white pigment includes a substrate and a first white metal oxide layer formed on the substrate. The second white pigment include a substrate and a second white metal oxide layer formed on the substrate, wherein the second white pigment has a colorimeter value that is different from that of the first white pigment.

In the composite white pigment according to the first embodiment of the present disclosure, the minimum thickness of the white metal oxide layer of the second white pigment is greater by at least 60 nm than the maximum thickness of the white metal oxide layer of the first white pigment. The thickness of the white metal oxide layer may vary, for example, may have about 80 nm, 120 nm, 140 nm, or 160 nm. Tones of the pigments may be slightly different from each other depending on the thickness of the white metal oxide layer.

For example, when the white metal oxide layer in the first white pigment has a thickness of 60 to100 nm, the thickness of the white metal oxide layer included in the second white pigment may have 120 to 260 nm thickness which is larger by at least 60 nm than the maximum thickness of the white metal oxide layer of the first white pigment. The pigments with different white tones may be mixed with each other to achieve higher whiteness.

In the composite white pigment according to the second embodiment of the present disclosure, for example, regarding the first white pigment, when the thickness of the substrate is between 200 and 250 nm, and the thickness of the white metal oxide layer is between 60 and 100 nm, the first white pigment has the green tone. To the contrary, regarding the second white pigment, when the thickness of the substrate is 300 to 350 nm, and the thickness of the white metal oxide layer is between 60 and 100 nm, the second white pigment has a red tone. When the white pigment of the green tone is mixed with the white pigment of the red tone, whiteness of the mixture can be improved as compared with only green tone white pigment or only red tone white pigment.

In another example, for example, in the composite white pigment according to the present disclosure, a white pigment with a white metal oxide layer of a thickness of about 60 nm and a white pigment with a white metal oxide of a thickness of about 100 nm may be mixed with each other.

In this connection, in the composite white pigment according to the first embodiment of the present disclosure, the minimum thickness of the substrate of the second white pigment is greater than the maximum thickness of the metal oxide layer of the first white pigment by at least 50 nm. In one example, when the thickness of the substrate of the first white pigment is in a range of 200 to 250, the substrate included in the second white pigment has a 300 to 350 nm thickness which is greater than the maximum thickness of the first white pigment substrate by at least 50 nm. When the substrate thickness difference therebetween is greater than or equal to 50 nm, rendered tones thereof may be different therebetween. Thus, mixing the first and second white pigments may allow the higher whiteness to be realized.

For example, in the first white pigment, when the thickness of the white metal oxide layer is about 80 nm, and when the thickness of the substrate is 200 to 250 nm, the green tone is rendered. To the contrary, in the second white pigment, when the thickness of the white metal oxide layer is about 80 nm and when the thickness of the substrate is 300 to 350 nm, the red tone is rendered. When the white pigment of the green tone is mixed with the white pigment of the red tone, whiteness can be improved as compared with only green tone white pigment or only red tone white pigment.

The composite white pigment according to the third embodiment of the present disclosure may be a preferred example of the composite white pigment according to the second embodiment, where the first white pigment and second white pigment are mixed with each other, each of which has a structure shown in FIG. 2.

In this case, when the thickness of the first high refractive layer is T1 and the thickness of the second high refractive layer is T2, $2T1 > T2 \geq T1$ for the first white pigment, while $3T1 \geq T2 \geq 2T1$ for the second white pigment.

That is, provided that the thickness of the first high refractive layer 220 is T1, and the thickness of the second high refractive layer 240 is T2, the thickness of the second high-refractive layer 240 may be 1 to 2 times larger than the thickness of the first high-refractive layer 220 ($1 < T2 \leq 2$). In this case, white having the green tone can be realized at a specific substrate thickness. Alternatively, the thickness of the second high-refractive layer 350 may be 2 to 3 times greater than the thickness of the first high-refractive layer 320 ($2 < T2 \leq 3$). In this case, white having the red tone can be realized at a specific substrate thickness. When the thickness of the substrate varies, the tone may vary slightly. Thus, adjusting the thickness ratio of the thickness of the second high refractive layer to the thickness of the first high refractive layer may allow various tones-rendering white pigments to be realized.

Further, the white pigment according to the present disclosure may be achieved by mixing a first white pigment in which the thickness of the second high-refractive layer 350 may be 1 to 2 times larger than the thickness of the first high-refractive layer 320 with a second white pigment in which the thickness of the second high refractive layer 350 is 2 to 3 times larger than the thickness of the first high refractive layer 320 at a weight ratio of about 80:20 to 20:80. In this case, the mixture may exhibit excellent whiteness while having a high gloss.

In this case, the composite white pigment may include at least two groups of substrates having thickness differences of 50 nm or greater as in the first embodiment.

In the composite white pigments according to the first to third embodiments, the white metal oxide layers having the same material and thickness are coated on the substrates, the tones of whites rendered by the composite white pigments may vary depending on the thicknesses of the substrates. When the same substrate thickness is used and the white metal oxide layers of the same material are coated on the substrates, the tones of whites rendered by the composite white pigments may vary depending on the thickness of the white metal oxide layer. Thus, the inventors of the present disclosure have concluded that when the white pigments having different white tones are mixed with each other, mixed white colors could be realized. Those mixed white colors may lead to high gloss and whiteness.

Preferably, each of the first white pigment and the second white pigment may be contained in an amount of 20 wt % or more. In other words, all of the white pigments having different tones are contained at a certain amount or greater, so that the reliability in rendering the high gloss and high whiteness can be enhanced.

The white pigment production method according to the present disclosure may include, for the structure shown in FIG. 1, a step of producing slurry in which substrates are dispersed, and forming a high-refractive layer on the surface of each of the substrates dispersed in the slurry. For the structure shown in FIG. 2, the white pigment production method according to the present disclosure may include producing a slurry in which the substrates are dispersed, forming a first high refractive layer on the surface of each of the substrates dispersed in the slurry, forming a low-refractive layer on the first high refractive layer, and forming a second high refractive layer on the low-refractive layer.

For varying the substrate thickness, substrates of various thicknesses may be dispersed in the slurry production step. Alternatively, a first white pigment may be produced using a substrate of a specific thickness, and a second white pigment may be produced using a substrate of a different thickness from the specific thickness, and then, the first and second pigments may be mixed with each other.

For varying the thickness of the white metal oxide layer, the concentration of the $TiO_2$ precursor solution (for example, $TiCl_4$ solution) to be added to the slurry may vary or the titration time may vary. Then, the first white pigment and second white pigment may be produced using the white metal oxide layers having varying thicknesses and then mixed with each other.

As described above, the composite white pigment according to the present disclosure has excellent white aesthetics, and, accordingly, may be applied to products such as paints, plastics, cosmetics and the like.

PRESENT EXAMPLES

Hereinafter, configurations of the present disclosure will be described in more detail using the preferred Present Example of the present disclosure. However, the Present Example is merely a preferred implementation of the present disclosure and should not be construed as limiting the present disclosure.

Contents as not described herein may be sufficiently technically inferred by those skilled in the art, and descriptions thereof will be omitted.

1. Production of White Pigment

COMPARATIVE EXAMPLE 1

100 g of synthetic mica flake having a thickness of 350 nm to 700 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 170 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 30 minutes.

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder.

PRESENT EXAMPLE 1

100 g of synthetic mica flakes having a thickness of 350 nm to 700 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 170 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 30 minutes.

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder.

The amount of $TiCl_4$ solution was increased using the above method to obtain pigment powders having gold, red and blue tones.

The white powders obtained by the above method are mixed with each other to obtain the white pigment powders rendering various tones.

PRESENT EXAMPLE 2

(1) Production Example 2-1

100 g of synthetic mica flakes having a thickness of 200 nm to 250 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 120 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 30 minutes.

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder rendering a green tone.

(2) Production Example 2-2

100 g of synthetic mica flakes having a thickness of 300 nm to 350 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 110 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 30 minutes.

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder rendering a red tone.

(3) Production Example 2-3

The white powders as obtained in Production Example 2-1 and Production Example 2-2 were mixed with each other in a weight ratio of 1:1 to obtain white pigment powders. This is called Present Example 2.

PRESENT EXAMPLE 3

(1) Production Example 3-1

100 g of synthetic mica flakes having a thickness of 350 nm to 750 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 130 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 10 minutes and then the pH thereof was adjusted to 7.5 with 20% NaOH diluent (first high refractive layer formation).

Then, 1,200 g of $MgO.SiO_2$ solution (3.5% by weight of $MgO.SiO_2$) was weighed, and added to the slurry in a titrated manner at a constant rate over 4 hour. The pH thereof was kept constant at 7.5 using an HCl solution. Thereafter, the pH of the slurry was adjusted to 1.7 by adding an HCl solution thereto, and the mixture was further refluxed and stirred for 15 minutes (Formation of low-refractive layer).

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 200 g of $TiCl_4$ solution (33% by weight of $TiCl_4$) was weighed and added to the slurry in a titrated manner at a constant rate over 6 hour. The pH thereof was kept constant at 1.7 using 30% NaOH diluent. After the titration, the mixture was refluxed for 30 minutes (second high refractive layer formation).

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder rendering a light green tone.

(2) Production Example 3-2

100 g of synthetic mica flakes having a thickness of 350 nm to 750 nm was added to 2 L demineralized water and then the mixture was stirred to form a slurry. Next, the slurry was heated to 75 degrees C., and then the pH of the slurry was adjusted to 1.7 by adding an HCl solution thereto.

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 130 g of $TiCl_4$ solution (33% by weight of $TiCl_4$) was weighed and added to the slurry in a titrated manner at a constant rate over 3 hour. The pH thereof was kept constant at 1.7 using 30% NaOH diluent. After the titration, the mixture was refluxed for 10 minutes and then the pH thereof was adjusted to 7.5 with 20% NaOH diluent (first high refractive layer formation).

Then, 1,200 g of $MgO.SiO_2$ solution (3.5% by weight of $MgO.SiO_2$) was weighed, and added to the slurry in a titrated manner at a constant rate over 4 hour. The pH thereof was kept constant at 7.5 using an HCl solution. Thereafter, the pH of the slurry was adjusted to 1.7 by adding an HCl solution thereto, and the mixture was further refluxed and stirred for 15 minutes (Formation of low-refractive layer).

Next, 27 g of $SnCl_4$ solution (11% by weight of $SnCl_4$) was weighed and added to the slurry in a titrated manner at a constant rate over 1 hour. The pH thereof was kept constant at 1.7 using 30% NaOH diluent.

Next, 300 g of $TiCl_4$ solution (33% by weight of $TiCl_4$) was weighed and added to the slurry in a titrated manner at a constant rate over 8 hour. The pH thereof was kept constant at 1.7 using 30% NaOH diluent. After the titration, the mixture was refluxed for 30 minutes (second high refractive layer formation).

After the refluxing, the final slurry was filtered and dehydrated and washed twice with demineralized water, and then dried at 120 degrees C. for 10 hours to obtain an intermediate product in a powder form.

Then, the obtained intermediate product was calcined at 800 degrees C. for 12 minutes to obtain a white pigment powder rendering a light red tone.

(3) Production Example 3-3

The white powders as obtained in Production Example 3-1 and Production Example 3-2 were mixed with each other in a weight ratio of 1:1 to obtain white pigment powders. This is called Present Example 3.

PRESENT EXAMPLE 4

White powders were obtained in the same manner as Production Example 3-1 and Production Example 3-2 except for using a plate type alumina flake with a thickness of 200 nm to 250 nm instead of the synthetic mica flake (Production Example 4-1, and Production Example 4-2). Then, the white powders as obtained in Production Example 4-1 and Production Example 4-2 were mixed with each other at a weight ratio of 1:1 to obtain white pigment powders (Production Example 4-3).

2. Property Evaluation

The physical properties according to Comparative Example 1 and Present Examples 1 to 4 were evaluated as follows.

(1) Saturation Evaluation

Table 1 shows colorimeter values (a*, b*) of the white pigments according to Production Examples 3-1, 3-2 and 3-3, and Production Examples 4-1, 4-2 and 4-3.

Table 2 shows the colorimeter values (a*, b*) of the white pigments according to Comparative Example 1 and Present Example 1 to 4. Colorimeter values were measured with Konika Minolta Chroma meter CR-400 D65. a* represents the intensity of red, b* represents the intensity of yellow. Δa* and Δb* represent changes in the colorimeter values for the Present Examples 1 to 4 relative to the Comparative Example and changes in the colorimeter values for Present Example 4 relative to the Present Example 2.

TABLE 1

| Examples | L* | a* | b* |
|---|---|---|---|
| Production Example 3-1 | 85.86 | −5.22 | −3.55 |
| Production Example 3-2 | 70.46 | 9.55 | −2.87 |
| Present Example 3 | 79.80 | −1.83 | −3.33 |
| Production Example 4-1 | 87.92 | −4.74 | −1.81 |
| Production Example 4-2 | 71.61 | 6.29 | −6.06 |
| Present Example 4 | 81.79 | −1.64 | −2.99 |

As shown in Table 1, in Production Examples 3-1 and 3-2, when the substrates have the same specific thickness, the white powders having a specific tone is obtained because of a low rendered color mixed level due to high saturation. Thus, mixing powders having different substrate thicknesses may control the tone of the white powders.

Production Example 3-1 is directed to the white powders with a light green tone, while Production Example 3-2 is directed to the white powders with a light red tone. It may be seen that these two types powders are mixed with each other such that the rendered colors are mixed with each other to obtain the white powder having a* and b* values close to zero and thus having enhanced whiteness.

In Present Example 4, it may be seen that the powders having a light green tone and the powders having a red tone are mixed with each other such that the rendered colors are mixed with each other to obtain the white powder having a* and b* values close to zero and thus having enhanced whiteness.

TABLE 2

| Examples | L* | a* | b* | Δa* | Δb* |
|---|---|---|---|---|---|
| Comparative Example 1 | 75.90 | −2.32 | −5.38 | — | — |
| Present Example 1 | 62.62 | −0.44 | −4.00 | +1.88 | +1.38 |
| Present Example 2 | 67.45 | −2.30 | −4.93 | +0.02 | +0.45 |
| Present Example 3 | 79.80 | −1.83 | −3.33 | +0.49 | +2.05 |
| Present Example 4 | 81.79 | −1.64 | −2.99 | +0.68 | +2.39 |
| Present Example 4 relative to Present Example 2 | | | | +0.66 | +1.94 |

Referring to Table 2, Comparative Example 1 is directed to a general white pearl pigment structure using a substrate having a constant thickness.

In Present Example 1, the whiteness is increased by mixing the powders having the metal oxide layers of different thicknesses on the same substrate as in Comparative Example 1 such that the rendered colors are mixed with each other to achieve enhanced whiteness.

In Present Example 2, the change of Δb* value is relatively smaller compared to Comparative Example 1, such that the blue tone is decreased and thus whiteness is enhanced.

In Present Example 3, the gloss increases slightly compared with Comparative Example 1, and the change of each of Δa* and Δb* values is relatively smaller compared to Comparative Example 1, such that the whiteness is enhanced.

In Present Example 4, the gloss becomes slightly higher compared with Comparative Example 1, and the change of each of Δa* and Δb* values is relatively smaller compared to Comparative Example 1, such that the whiteness is enhanced.

Further, in Present Example 4, the gloss increases slightly compared to Present Example 2, and the change of each of Δa* and Δb* values is relatively smaller compared to Present Example 2, such that the whiteness is enhanced.

APPLICATION EXAMPLE

The following provides a description of an application example in which the white pigment as obtained in the Present Example 3 is applied to paints, plastics, inks and cosmetics.

(1) Example for Use in Paints

This is an example for use of the pigment in automotive surface coatings.
{Basic Coating Composition}
[Polyester Resin]
HiQ base coloring transparent (BC-1000) NOROO Paint & Coatings Co., Ltd
HiQ LV thinner (DR-950WS) NOROO Paint & Coatings Co., Ltd
4 parts by weight of white pigments as obtained in Present Example 3 and 96 parts by weight of the polyester resin composition were mixed with each other. Then, 100 parts by weight of a diluent for a polyester resin was added to the mixture. The concentration of the mixture was lowered for spray coating (application for 14 to 16 seconds using a Ford cup #4 at 25 degrees C.). Then, the mixture was applied using the spray coating to form a base paint film. An uncolored surface transparent paint of a following composition was applied on the base paint film.
{Surface Transparent Paint}
HiQ Ultraclear NOROO Paint & Coatings Co., Ltd
HiQ Ultraclear curing agent (CCH-100) NOROO Paint & Coatings Co., Ltd
After the surface coating, the paint was exposed to air at 40 degrees C. for 30 minutes, and was heated for curing at 130 degrees C. for 30 minutes.

(2) Examples for Use in Plastic

The following is an example of the pigment composition used to color plastics.
Polyethylene resin (pellets): 70 parts by weight
White pigment as obtained in Present Example 3: 1 parts by weight
Zinc Stearate: 0.2 parts by weight
Liquid paraffin: 0.1 parts by weight
The pellets containing the composition were dried and blended and extruded and molded.

(3) Examples for Use in Cosmetics

The following is an example of a composition for lip-coloring cosmetics.
Hydrogenated Castor Oil—37 parts by weight
Octyldodecanol—10 parts by weight
Diisostearyl Malate—20 parts by weight
Ceresin—5 parts by weight
Euphorbia Cerifera (Candelilla) Wax—5 parts by weight Dipentaerythrityl Hexahydroxystearate/Hexastearate/Hexarosinate—18.5 parts by weight Copernicia Cerifera (Carnauba) Wax—3 parts by weight Isopropyl Lanolate—1 parts by weight VP/Hexadecene Copolymer—1 parts by weight White pigment as obtained in Present Example 3: proper content Antioxidants, preservatives and fragrances: small amounts Lipstick was formed from the composition.

Although the present disclosure has been described with reference to the embodiments, various modifications and variations may be made thereto by those skilled in the art. Unless such changes and modifications depart from the scope of the present disclosure, they are included in the present disclosure. Accordingly, the scope of the present disclosure should be determined by the claims set forth below.

What is claimed is:

1. A composite white pigment comprising:
   a first white pigment including:
     a substrate; and
     a white metal oxide layer formed on the substrate; and
   a second white pigment including:
     a substrate; and
     a white metal oxide layer formed on the substrate,
   wherein the second white pigment has a colorimeter value different from a colorimeter value of the first white pigment.

2. The composite white pigment of claim 1, wherein a minimum thickness of the substrate of the second white pigment is larger than a maximum thickness of the substrate of the first white pigment by 50 nm or more.

3. The composite white pigment of claim 2, wherein a thickness of the substrate of the first white pigment ranges from 200 nm to 250 nm, and a thickness of the substrate of the second white pigment of ranges from 300 nm to 350 nm.

4. The composite white pigment of claim 1, wherein the white metal oxide layer of the first white pigment or the white metal oxide layer of the second pigment includes:
   a first high refractive layer comprising $TiO_2$, wherein the first high refractive layer is on a surface of the substrate of the first white pigment or a surface of the substrate of the second white pigment;
   a low-refractive layer comprising a material having a refractive index lower than a refractive index of $TiO_2$, wherein the low refractive layer is on the first high refractive layer; and
   a second high refractive layer comprising $TiO_2$, wherein the second high refractive layer is on the low refractive layer.

5. The composite white pigment of claim 4, wherein when a thickness of the first high-refractive layer is T1 and a thickness of the second high-refractive layer is T2, T2>T1.

6. The composite white pigment of claim 1, wherein a minimum thickness of the white metal oxide layer of the second white pigment is larger than a maximum thickness of the white metal oxide layer of the first white pigment by 60 nm or more.

7. The composite white pigment of claim 6, wherein a thickness of the white metal oxide layer of the first white pigment ranges from 30 nm to 80 nm, and wherein a thickness of the white metal oxide layer of the second white pigment ranges from 100 nm to 160 nm.

8. The composite white pigment of claim 1, wherein the white metal oxide layer of the first white pigment or the white metal oxide layer of the second white metal oxide layer includes:
   a first high refractive layer comprises $TiO_2$, wherein the first refractive layer is on a surface of the substrate of the first white pigment or a surface of the substrate of the second white pigment;
   a low-refractive layer comprising a material having a refractive index lower than a refractive index of $TiO_2$, wherein the low-refractive layer is on the first high refractive layer; and
   a second high refractive layer comprising $TiO_2$, wherein the second high refractive layer is on the low-refractive layer,
   wherein when a thickness of the first high refractive layer is T1 and a thickness of the second high refractive layer is T2, 2T1>T2≥T1 for the first white pigment, while 3T1≥T2≥2T1 for the second white pigment.

9. The composite white pigment of claim 4, wherein the low-refractive layer comprises at least one selected from the group consisting of $SiO_2$ and $MgO \cdot SiO_2$.

10. The composite white pigment of claim 1, wherein the substrate of the first white pigment or the substrate of the second white pigment is natural mica, synthetic mica, glass flake or alumina flake.

11. An interference pigment comprising the composite white pigment according to claim 1, wherein the composite white pigment is used in at least one selected from the group consisting of paints, printing inks, floor plates, wallpaper, special paper, plastic, leather, accessories, cosmetics, ceramics and artificial marble.

12. The composite white pigment of claim 8, wherein the low-refractive layer at least one selected from the group consisting of $SiO_2$ and $MgO \cdot SiO_2$.

* * * * *